United States Patent
Huang

(10) Patent No.: US 10,675,318 B2
(45) Date of Patent: Jun. 9, 2020

(54) ANTIOXIDATIVE ACTIVITY PROMOTING COMPOSITION

(71) Applicant: Fu-Hsing Huang, Taichung (TW)

(72) Inventor: Fu-Hsing Huang, Taichung (TW)

( * ) Notice: Subject to any disclaimer, the term of this patent is extended or adjusted under 35 U.S.C. 154(b) by 0 days.

(21) Appl. No.: 16/169,641

(22) Filed: Oct. 24, 2018

(65) Prior Publication Data
US 2020/0129576 A1  Apr. 30, 2020

(51) Int. Cl.
| | |
|---|---|
| *A61K 36/00* | (2006.01) |
| *A61K 36/41* | (2006.01) |
| *A61K 36/77* | (2006.01) |
| *A61P 3/04* | (2006.01) |
| *A61K 31/05* | (2006.01) |
| *A61K 31/661* | (2006.01) |

(52) U.S. Cl.
CPC ............. *A61K 36/41* (2013.01); *A61K 31/05* (2013.01); *A61K 31/661* (2013.01); *A61K 36/77* (2013.01); *A61P 3/04* (2018.01)

(58) Field of Classification Search
None
See application file for complete search history.

(56) References Cited

U.S. PATENT DOCUMENTS

| | | | |
|---|---|---|---|
| 9,737,580 B2 | 8/2017 | Reynolds | |
| 2012/0165412 A1* | 6/2012 | van der Beek | ........... A23L 2/52 514/733 |
| 2016/0038552 A1* | 2/2016 | Bredesen | ............... A61K 36/41 424/400 |

FOREIGN PATENT DOCUMENTS

TW   I441643   6/2014

* cited by examiner

*Primary Examiner* — Qiuwen Mi
(74) *Attorney, Agent, or Firm* — Muncy, Geissler, Olds & Lowe, P.C.

(57) ABSTRACT

A composition for promoting antioxidative activity includes an effective dose of *Rhodiola* extract, an alpha-Glycerophosphocholine (alpha-GPC), and a pharmaceutically acceptable vehicle or salt thereof. Based on animal experiments, the combination of *rhodiola* extract and alpha-Glycerophosphocholine provides high antioxidative activity.

9 Claims, 2 Drawing Sheets

Normal Group

Control Group

First Experimental Group

Second Experimental Group

Third Experimental Group

Fourth Experimental Group

Normal Group

Control Group

First Experimental Group

Second Experimental Group

Third Experimental Group

Fourth Experimental Group

ANTIOXIDATIVE ACTIVITY PROMOTING COMPOSITION

BACKGROUND OF THE INVENTION

1. Field of the Invention

The present invention relates to compositions, and more particularly, to an antioxidative activity promoting composition.

2. Description of the Related Art

Human growth hormone (HGH) is a type of peptide hormone secreted by pituitary gland. The HGH in human body assists the repairing and regeneration of tissue cells, maintains the activity of body organs, increases bone density, and lowers body fat and cholesterol. However, the secretion of HGH in human body gradually decreases after the age of 25. Also, with the effects of pressure in daily life and the environment deterioration, body functions will be declining and aging.

The aforementioned body fat and body function aging issues are able to be improved through diet improvement and exercising. Medication will be introduced when such manners fail to bring up mitigation. Also, for achieving the objective of retraining formation of body fat and postponing body aging, researchers have executed various biochemical experiments. Based on experiments, it is discovered that *rhodiola* plant provides beneficial functions against oxygen deficit and fatigue, and also helps postponing body aging and adjusting endocrine system. Therefore, various compound prescriptions includes the content of *rhodiola*.

Referring to US9737580B2, compositions and methods for enhancing brain function are disclosed, wherein the composition includes huperzine A, vinpocetine, acetyl-L-carnitine, and *rhodiola*. According to clinical experiments, a preferable ratio of the combination thereof improves emotional recognition and helps controlling body weight. However, the composition mainly improves the brain function to enhance memory and emotional recognition. Therefore, it fails to proof that such composition is able to achieve the aging postponement effect.

Referring to Taiwan patent 1441643, a composition for adjusting blood lipid and protection cardiovascular system is disclosed, wherein the composition includes compound *rhodiola* powder, monascus, phytol, natto, and vitamin B complex. Based on animal experiments, such composition achieves blood lipid adjustment and cardiovascular system protection functions. Also, with a certain dosage ratio, an obvious body weight reduction effect is achieved. However, such art does not prove that the composition achieve an antioxidative function.

SUMMARY OF THE INVENTION

The present invention mainly aims at resolving the issue that prior arts are unable to improve the body fat accumulation and body function aging at the same time.

For achieving the aforementioned objectives, an antioxidative activity promoting composition is provided. The composition includes an effective amount of *rhodiola* extract, a alpha-Glycerophosphocholine (alpha-GPC), and a pharmaceutically acceptable vehicle or salt thereof.

Also, a method for treating obesity by use of composition above is provided by another embodiment of the present invention. An experiment subject receives an effective oral dosage of a composition formed of *rhodiola* extract, alpha-Glycerophosphocholine, and a pharmaceutically acceptable vehicle or salt thereof. With the combination of *rhodiola* extract and alpha-Glycerophosphocholine, the body fat formation of the subject is restrained, and the antioxidative activity of the subject is improved.

Based on experiments of fat formation and body aging induction, *rhodiola* extract and alpha-Glycerophosphocholine are proved to be effective on reducing the body weight and body fat of animals. Moreover, the antioxidative activity in the animal body is increased. Therefore, the objectives of reducing body fat and postponing body aging are achieved.

DETAILED DESCRIPTION OF THE INVENTION

Figure 1:
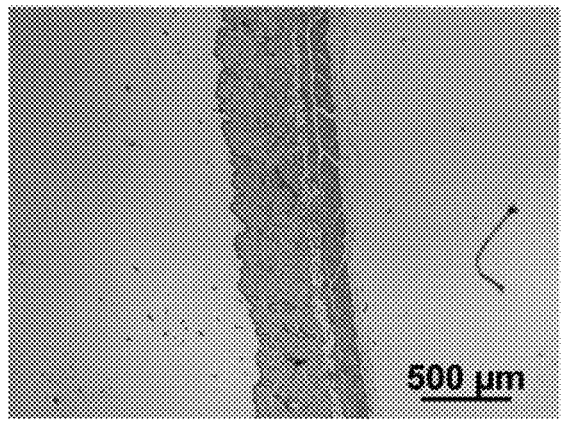
FIG. 1 is an image illustrating the stained hair follicles and subcutaneous fat of skin tissue of each group of experiment subjects.
Figure 1:
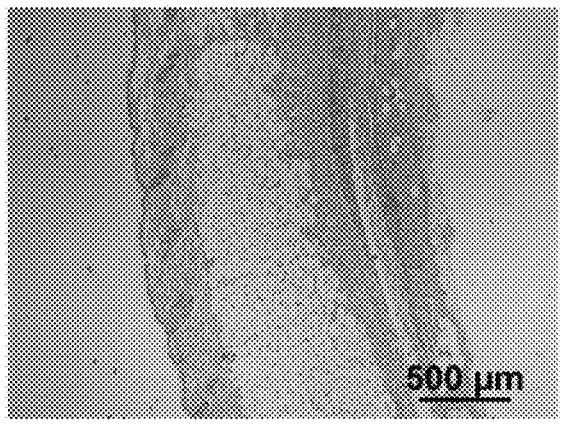
Figure 1:
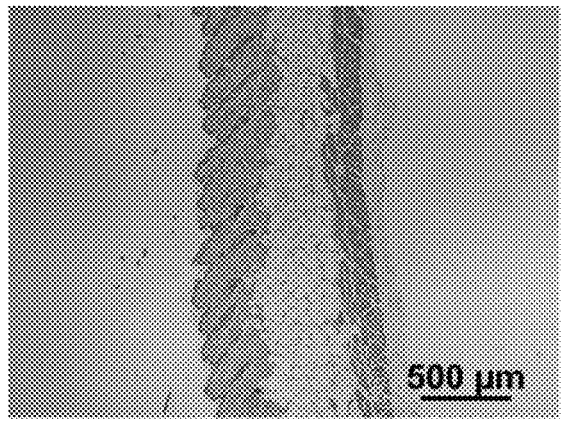
Figure 1:
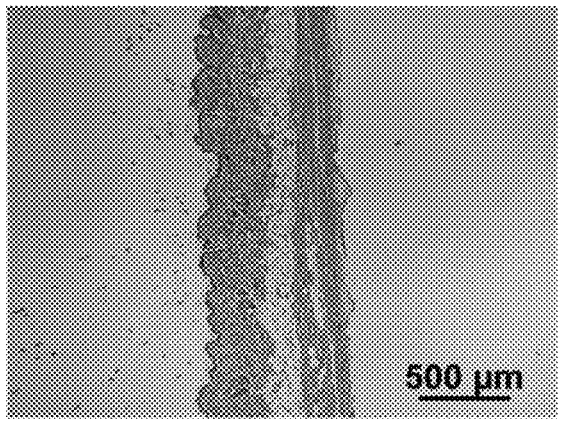
Figure 1:
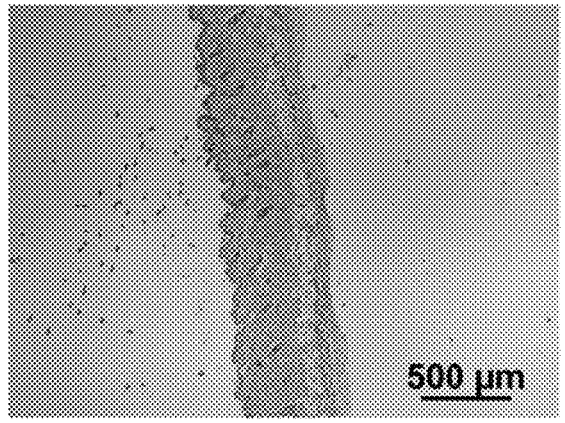
Figure 1:
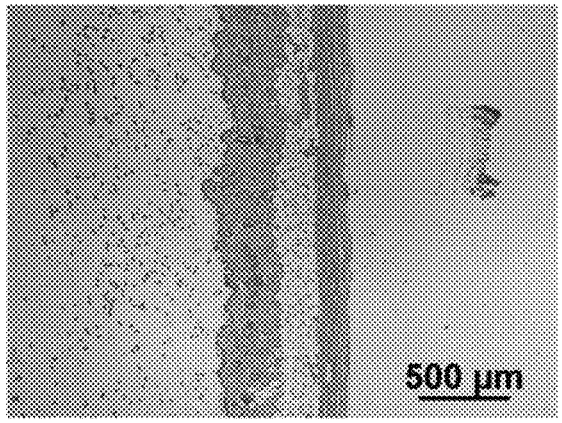

The aforementioned and further advantages and features of the present invention will be understood by reference to the description of the preferred embodiment in conjunction with the accompanying drawings.

The present invention provides an antioxidative activity promoting composition formed of *rhodiola* extract, alpha-Glycerophosphocholine (alpha-GPC), and a pharmaceutically acceptable vehicle or salt thereof.

*Rhodiola* plant is a perennial plant or a shrub plant. A *rhodiola* extract includes abundant antibacterial and anti-inflammatory content, such as hyoscine and kaempferol. Also, *rhodiola* provides beneficial functions against oxygen deficit, and also helps resisting fatigue, postponing body aging and adjusting endocrine system.

Alpha-Glycerophosphocholine (alpha-GPC) is a small molecular nutrient, which mainly exists in human body cell and breast milk, or is extracted from non-genetically modified soybean through deacetylation and specific ion exchanging technique. Research proves that alpha-GPC helps the growth and regeneration of tissue, assists the vitalization of body organs, restores the circulation lacking brain function, and maintains the physical functions such as concentrating, focusing, and memory ability of brain. Based on clinical experiments, oral administration of alpha-GPC increases the concentration of choline and acetylcholine in blood, thereby lowering the concentration of cortisone and further increasing the concentration of HGH in the human body.

Therein, the ratio between the *rhodiola* extract and the alpha-GPC ranges from 1:1 to 1:6. In a preferred embodiment of the present invention, the ratio between the *rhodiola* extract and the alpha-GPC is 1:3.

Also, the composition further comprises resveratrol and guarana content. Resveratrol exists in various plants, such as mulberry, peanut, and grape, especially abundantly exists in grape. According to research, resveratrol has great antioxidative activity. Resveratrol not only protects human body from damage of free radical, but also produces antitoxin when the plant faces environmental stress, fungal and bacterial infections.

Guarana content includes stimulating substances, which increase the mental and muscular resistance and endurance, also help reducing physical tiredness after exercise. Caffeine in Guarana includes xanthine, which facilitates an efficient and stable thinking ability.

The composition of the present invention is allowed to be prepared in a powder, granular, or liquid form. Also, the composition is able to be processed into capsule form for facilitating oral administration, wherein the capsule form includes an animal based capsule made of gelatin and a vegetable based capsule made of sodium carboxymethyl cellulose.

The term "pharmaceutically acceptable salt" includes water soluble and insoluble salt, which maintains the biological effect and property of the composition. The term "pharmaceutically acceptable vehicle" refers to a substance, combination, or medium agent for carrying the medication between organs or body parts in an organism, such as flavoring agent, enhancer, preservative, antioxidant, chelating agent, penetrant, lubricant, tablet adjuvant, colorant, humectant, bonding agent, and carrier agent with equivalent effects.

In the embodiment, animal experiments are used for proving the antioxidative activity promoting effects provided by the composition of the present invention.

Animal Experiments

I. Animal Rearing:

The subject of the experiment is provided from Laboratory Animal Center of NHRI in Taiwan. The subject is sixty C57BL/6(B6) male mice aging from 6-8 weeks that are divided into six groups, wherein each group includes ten mice. The initial weight of the each mice is 20 grams. Each group of subjects are reared in an animal house under a temperature of 22±2° C., wherein the light duration and dark duration of the animal house is 12 hours, respectively. Based on the fact that the subjects usually take food during dark duration, the time point for removing the food is at the transition from dark duration into light duration. Subjects will keep an empty stomach for 12±2 hours.

II. Feeding:

Subjects are orally fed with high-fat food and injected with D-galactose. Notably, the high-fat food is applied for inducing obesity of the subjects. Injection of overdose of D-galactose causes a large amount of reactive oxygen species to be produced in the subject body, so as to break the balance status of the reactive oxygen species in the subject body, therefor inducing the peroxidation in the subject body.

III. Medication Administration:

The subjects are divided into six groups according to the weight distribution, wherein each group includes ten subjects. Each subject is fed with high-fat food in the animal room and injected with D-galactose. Then, the subjects are orally administered with the combination of *rhodiola* extract and alpha-Glycerophosphocholine in accordance with an embodiment of the present invention. The experiment is carried out for twelve weeks, wherein the subject is weighted once a week with records made. The term "administered" herein refers to directly providing the combination or the pharmaceutically acceptable salt of the combination, such that an equivalent amount of active combination is formed in the subject body.

The groups of the experiment are mainly divided into a normal group, a control group, a first experimental group, a second experimental group, a third experimental group, and a fourth experimental group. In the normal group, the subjects takes an ordinary food freely and administered with 10 ml/kg germ-free RO water. In the control group, the subjects take high-fat food freely and injected with 0.3-1.2 g/kg bw D-galactose by subcutaneous injection from neck and back body part. Also, the subjects are administered with 10 ml/kg germ-free RO water. In the first experimental group, the subjects take high-fat food freely and injected with 0.3-1.2 g/kg bw D-galactose by subcutaneous injection from neck and back body part. Also, the subjects are administered with one dosage of *rhodiola* extract, wherein the dosage amount of *rhodiola* extract is 88.4 mg/kg bw per day. In the second experimental group, the subjects take high-fat food freely and injected with 0.3-1.2 g/kg bw D-galactose by subcutaneous injection from neck and back body part. Also, the subjects are administered with low dosage of the combination of the present invention (*rhodiola* extract: alpha-GPC=1:1). Therein, the effective dosage amount of the combination of *rhodiola* extract and alpha-GPC is 187 mg/kg bw per day. Based on a same body area ratio comparison, the dosage amount equals to a dosage of 0.91 g per day for human body. In the third experimental group, the subjects take high-fat food freely and injected with 0.3-1.2 g/kg bw D-galactose by subcutaneous injection from neck and back body part. Also, the subjects are administered with medium dosage of the combination of the present invention (*rhodiola* extract: alpha-GPC=1:3). Therein, the effective dosage amount of the combination of *rhodiola* extract and alpha-GPC is 384.4 mg/kg bw per day. Based on a same body area ratio comparison, the dosage amount equals to a dosage of 1.87 g per day for human body. In the fourth experimental group, the subjects take high-fat food freely and injected with 0.3-1.2 g/kg bw D-galactose by subcutaneous injection from neck and back body part. Also, the subjects are administered with high dosage of the combination of the present invention (*rhodiola* extract: alpha-GPC=1:6). Therein, the effective dosage amount of the combination of *rhodiola* extract and alpha-GPC is 680.4 mg/kg bw per day. Based on a same body area ratio comparison, the dosage amount equals to a dosage of 3.31 g per day for human body.

| Groups | High-fat food | D-galactose | Ratio of rhodiola extract and alpha-GPC | Effective amount of rhodiola extract and alpha-GPC combination |
|---|---|---|---|---|
| Normal group | – | – | – | – |
| Control group | + | + | – | – |
| First experimental group | + | + | Only rhodiola extract | 88.4 mg/kg bw per day |
| Second experimental group | + | + | 1:1 | 187 mg/kg bw per day |
| Third experimental group | + | + | 1:3 | 384.4 mg/kg bw per day |
| Fourth experimental group | + | + | 1:6 | 680.4 mg/kg bw per day |

Conversion of experimental dosage for animal and human body: The conversion of experimental dosage for animal and human body is carried out according to "Estimating the maximum safe starting dose initial clinical trials for therapeutics in adult healthy volunteers" declared in 2005 by US FDA. And with a 60 kg adult as the basis, during an animal experiment, the effective dosage amount is conversed based on the equivalent dosage of recommended intake amount/kg bw/day of human body.

Because animals will increase their food intake amount when the body weight increase, the two conversion methods above cause minor difference upon the intake amount of the tested sample for animals. Therefore, the two conversion methods are both applicable. The experimental groups and control group shall take food having approximately identical calories, protein, fat, calcium, minerals, or vitamin contents.

The recommended dosage amount conversed from the animal experiment result for human body: The most suitable effective dosage amount is acquired from the statistics of the animal experiment. When the dosage amount is presented with the unit of percentage (%), the same percentage of the amount in the total food intake amount (500 g net weight) in one day is considered as one dosage. For example, when the tested sample accounts for 1% of the food with the most optimal result acquired, the most optimal one dosage amount for human body to intake is defined as 1% (5 g). When the dosage amount is presented with the unit of "/kg bw", the one dosage amount for human body is such dosage amount multiplying 60 times.

IV. Sampling and Analyzing:

(A) Weight Variation:

In the experiment duration, the subjects is accurately weighted at least one time per week (preferably at the transition time turning from light to dark and prior to food feeding). The weight variation of each groups of subjects are observed. The conversion formula of weight is: weight change=later weight−initial weight.

TABLE 1 weight variation of each group

| Groups Weeks | Normal group | Control group | First experimental group | Second experimental group | Third experimental group | Fourth experimental group |
|---|---|---|---|---|---|---|
| | | | | Weight (g) | | |
| Week0 | 22.0 ± 1.2$^a$ | 22.5 ± 1.0$^a$ | 22.1 ± 1.4$^a$ | 21.7 ± 1.3$^a$ | 22.2 ± 1.1$^a$ | 22.0 ± 0.6$^a$ |
| Week1 | 22.5 ± 1.1$^a$ | 25.1 ± 1.4$^b$ | 24.7 ± 1.6$^b$ | 24.1 ± 1.3$^b$ | 24.0 ± 0.8$^b$ | 24.9 ± 1.2$^b$ |
| Week2 | 23.5 ± 1.3$^a$ | 26.4 ± 1.6$^c$ | 25.3 ± 1.4$^{bc}$ | 24.9 ± 1.1$^b$ | 25.0 ± 1.0$^b$ | 25.5 ± 1.2$^{bc}$ |
| Week3 | 23.7 ± 1.5$^a$ | 27.2 ± 1.6$^c$ | 25.6 ± 1.6$^b$ | 25.3 ± 1.4$^b$ | 25.2 ± 0.7$^b$ | 25.7 ± 1.3$^b$ |
| Week4 | 25.0 ± 1.8$^a$ | 28.6 ± 1.5$^c$ | 26.5 ± 1.9$^b$ | 26.3 ± 1.1$^{ab}$ | 26.0 ± 0.5$^{ab}$ | 27.0 ± 1.5$^b$ |
| Week5 | 26.5 ± 2.2$^a$ | 30.6 ± 1.7$^c$ | 27.6 ± 2.3$^{ab}$ | 27.4 ± 1.1$^{ab}$ | 26.8 ± 0.9$^{ab}$ | 28.3 ± 1.7$^{bc}$ |
| Week6 | 26.6 ± 2.2$^a$ | 31.4 ± 1.7$^c$ | 28.5 ± 2.5$^b$ | 27.6 ± 1.1$^{ab}$ | 27.2 ± 0.8$^{ab}$ | 28.8 ± 1.8$^b$ |
| Week7 | 26.9 ± 2.1$^a$ | 32.9 ± 2.0$^c$ | 29.5 ± 2.3$^b$ | 28.1 ± 1.1$^{ab}$ | 28.0 ± 0.7$^{ab}$ | 29.6 ± 2.0$^b$ |
| Week8 | 27.0 ± 2.1$^a$ | 33.5 ± 2.2$^c$ | 29.8 ± 2.1$^b$ | 28.4 ± 1.3$^{ab}$ | 28.5 ± 1.0$^{ab}$ | 29.9 ± 2.0$^b$ |
| Week9 | 27.4 ± 2.2$^a$ | 36.0 ± 2.4$^c$ | 30.9 ± 2.2$^b$ | 29.6 ± 1.5$^b$ | 29.5 ± 1.3$^b$ | 31.1 ± 2.3$^b$ |
| Week10 | 27.9 ± 2.3$^a$ | 36.3 ± 2.4$^c$ | 31.0 ± 2.2$^b$ | 29.8 ± 1.4$^b$ | 30.0 ± 1.5$^b$ | 31.3 ± 2.7$^b$ |
| Week11 | 28.1 ± 2.3$^a$ | 37.2 ± 2.3$^c$ | 31.3 ± 2.3$^b$ | 30.5 ± 1.6$^b$ | 30.3 ± 1.7$^b$ | 31.9 ± 2.6$^b$ |
| Week12 | 28.2 ± 2.1$^a$ | 37.7 ± 2.2$^c$ | 31.6 ± 2.2$^b$ | 30.9 ± 1.7$^b$ | 30.6 ± 1.7$^b$ | 32.4 ± 2.6$^b$ |
| Weight gained | 6.3 ± 1.2$^a$ | 15.3 ± 1.8a | 9.5 ± 1.6$^{bc}$ | 9.2 ± 1.0$^{bc}$ | 8.4 ± 1.5$^b$ | 10.4 ± 2.26$^{bc}$ |

*$P < 0.05$,
**$P < 0.01$,
***$P < 0.001$

Referring to table 1, weight variations of each group of subjects in the embodiment are listed. Based on table 1, with the experiments proceeding on a weekly basis, average weight of all subjects stably rise, wherein the average weight of the control group subjects rise most significantly. However, regarding the second to fourth experimental groups, after administering the combination of the present invention, average weight gained by the subjects in those groups are obviously lower than the weight gained by the subjects in the control group. Especially, referring to the third experimental group, the average weight of the subjects are lower than the weight of subjects of control group by about 7 g. It is clearly that the composition of the *rhodiola* extract and alpha-GPC of the present invention is able to effectively reduce the weight of the subjects. Also, the greatest weight reduction occurs on the third experimental group, whose *rhodiola* extract and alpha-GPC combination ratio is 1:3.

(B) Weight Variation of Body Organs and Body Fat

Upon the sacrifice of the experimental animals, the epididymal adipose, the perirenal fat, and the mesenteric fat are carefully taken out from the peritoneal cavity to be accurately weighted, and the body fat percentage is then calculated. The calculation formula of body fat percentage is: body fat percentage=(body fat amount(g)/body weight(g))× 100%. In the calculation, body fact amount(g)=epididymal adipose(g)+perirenal fat(g)+mesenteric fat(g). The body fat amount measurement is carried by the same personnel for lowering the measurement error among the animals.

TABLE 2 weight variation of body organ and body fat of each group

| Groups Organs | Normal group | Control group | First experimental group | Second experimental group | Third experimental group | Fourth experimental group |
|---|---|---|---|---|---|---|
| | | | | Weight (g) | | |
| liver | 1.10 ± 0.07b | 1.11 ± 0.06b | 1.00 ± 0.07 a | 0.97 ± 0.08 | 1.02 ± 0.08 a | 1.02 ± 0.08 a |
| spleen | 0.06 ± 0.01a | 0.07 ± 0.01b | 0.07 ± 0.01 ab | 0.07 ± 0.01 | 0.06 ± 0.01 a | 0.07 ± 0.01 a |
| mesenteric fat | 0.16 ± 0.10a | 0.52 ± 0.15b | 0.32 ± 0.17 | 0.33 ± 0.22 | 0.31 ± 0.20 a | 0.30 ± 0.18 a |
| epididymal adipose | 0.40 ± 0.14a | 2.02 ± 0.34c | 1.24 ± 0.39 b | 1.07 ± 0.31 | 1.21 ± 0.22 b | 1.24 ± 0.32 b |

TABLE 2-continued weight variation of body organ and body fat of each group

| Groups Organs | Normal group | Control group | First experimental group | Second experimental group | Third experimental group | Fourth experimental group |
|---|---|---|---|---|---|---|
| | | | Weight (g) | | | |
| perirenal fat | 0.13 ± 0.08a | 0.96 ± 0.20c | 0.55 ± 0.23 b | 0.52 ± 0.18 | 0.55 ± 0.13 b | 0.58 ± 0.23 b |
| general fat | 0.68 ± 0.26a | 3.51 ± 0.57c | 2.11 ± 0.63 b | 1.93 ± 0.64 | 2.07 ± 0.50 b | 2.12 ± 0.63 b |
| body fat percentage | 2.4 ± 0.9 a | 9.3 ± 1.3 c | 6.7 ± 1.9 b | 6.2 ± 1.9 b | 6.7 ± 1.3 b | 6.5 ± 1.7 b |

*$P < 0.05$,
**$P < 0.01$,
***$P < 0.001$

Referring to table 2, weights variation of body organs and body fat of each group of subjects are listed. Based on table 2, after twelve weeks of experiment, all of the body fat percentage and general fat amount of the subjects rise, wherein the weights variation of the control group rise most significantly ($P<0.05$). However, referring to the second to fourth experimental group, after being administered with the combination of the present invention, the body fat percentage and the general fat amount of the subjects significantly lower ($P<0.05$). In other words, the combination of the present invention effectively restrains the formation of body fat and reduce obesity.

(C) Variation of Biochemical Values in the Blood

A blood biochemical analysis is carried out for analyzing various biochemical values related to the formation of body fat. The items of the biochemical analysis includes:

(i) Blood lipid: After fasting for 12 hours, the subjects are anesthetized with isofurane. Next, blood in the abdominal cavity artery is collected, and the serum of the collected blood is isolated by centrifugation. Next, the serum undergoes an analyze by a serum biochemical analyzer for detecting the concentration of triglyceride, cholesterol, low density lipoprotein (LDL), and high density lipoprotein (HDL) in the serum.

(ii) Liver lipid: After the collection of abdominal cavity artery blood, physiologic saline solution is used for rinsing the abdominal cavity. Next, chloroform-methanol extraction is applied for extracting the lipid from the body, and the concentration of triglyceride and cholesterol are determined.

(iii) Blood sugar: After the collection of abdominal cavity artery blood, the concentration of blood sugar is determined by enzymatic method and colorimetry.)

(iv) Kidney function: After the collection of abdominal cavity artery blood, the concentration of creatinine in blood is determined by enzymatic method and colorimetry.

TABLE 3 blood biochemical value variation of each group of subjects

| Groups | Normal group | Control group | First experimental group | Second experimental group | Third experimental group | Fourth experimental group |
|---|---|---|---|---|---|---|
| | | | Blood biochemical values | | | |
| blood sugar (mg/dL) | 214.8 ± 34.5a | 251.7 ± 26.2b | 246.0 ± 18.4ab | 243.9 ± 44.8ab | 231.3 ± 38.6ab | 231.8 ± 0.5ab |
| cholesterol (mg/dL) | 267.4 ± 63.5a | 415.4 ± 148.5b | 276.7 ± 88.3a | 292.1 ± 87.5a | 302.0 ± 69.4a | 299.5 ± 84.7a |
| creatinine (mg/dL) | 0.6 ± 0.2 ab | 0.7 ± 0.2 b | 0.7 ± 0.1 b | 0.6 ± 0.2 ab | 0.6 ± 0.1 ab | 0.5 ± 0.2 a |
| LDL (mg/dL) | 14.5 ± 3.7 ab | 39.1 ± 13.7 c | 19.0 ± 7.5 b | 9.9 ± 6.6 a | 13.6 ± 7.4 ab | 14.9 ± 10.8 ab |
| HDL (mg/dL) | 88.7 ± 14.6a | 158.3 ± 13.3b | 174.3 ± 17.2c | 164.1 ± 7.2bc | 167.6 ± 8.6bc | 68.4 ± 13.9bc |

*$P < 0.05$,
**$P < 0.01$,
***$P < 0.001$

Referring to Table 3, blood biochemical values variation are listed. Based on Table 3, after twelve weeks of experiment, blood sugar concentration of the control group subjects rise more significantly than that of the normal group subjects (P<0.05). However, blood sugar concentration of the subjects of the first to fourth experimental groups are slightly lower than that of the control group subjects. Cholesterol concentration of the subjects of the first to fourth experimental groups are significantly lower than that of the control group subjects (P<0.05). Creatinine concentration of the subjects of the first to third experimental groups are slightly lower than that of the control group subjects, and the creatinine concentration of the subjects of the fourth experimental groups is significantly lower than that of the control group subjects (P<0.05). LDL concentration of the subjects of the first to fourth experimental groups are significantly lower than that of the control group subjects (P<0.05). HDL concentration of the subjects of the first to fourth experimental groups are significantly higher than that of the control group subjects (P<0.05). Therefore, according to the experimental result of Table 3, the combination of the present invention effectively restrains various biochemical activity in the body related to the body fat formation, so as to effectively lower the body fat percentage.

(D) Blood Antioxidative Index Variation

Enzymatic method and colorimetry are applied for measuring the concentration of superoxide dismutase (SOD), GSH Px, and Glucose-6-phosphate dehydrogenase (G6PD) activity.

TABLE 4 blood antioxidative index variation of each group of subjects

| Groups | Normal group | Control group | First experimental group | Second experimental group | Third experimental group | Fourth experimental group |
|---|---|---|---|---|---|---|
| | | | Blood biochemical values | | | |
| SOD, U/mL | 2,153.0 ± 131.4$^c$ | 1,248.0 ± 112.7$^a$ | 1,365.3 ± 97.9$^b$ | 2,291.5 ± 128.1$^d$ | 2,223.0 ± 156.5$^{cd}$ | 2,298.5 ± 142.2$^d$ |
| GPx, U/L | 3,317.2 ± 197.5$^c$ | 1,778.0 ± 97.4$^a$ | 2,021.4 ± 112.7$^b$ | 3,261.2 ± 129.8$^c$ | 3,516.2 ± 281.8$^d$ | 3,381.6 ± 312.1$^{cd}$ |
| G6PD, mU/mL | 7.5 ± 0.6$^{bc}$ | 5.0 ± 1.2$^a$ | 7.6 ± 0.8$^{bc}$ | 7.2 ± 0.9$^b$ | 8.1 ± 1.0$^c$ | 7.4 ± 0.7$^{bc}$ |

*P < 0.05,
**P < 0.01,
***P < 0.001

Referring to Table 4, blood antioxidative index variation of each group of subjects are listed. Based on able 4, after twelve weeks of experiment, the SOD, GSH Px, and G6PD of the second to fourth experimental groups rise significantly (P<0.05) compared the control group, wherein the greatest increase of the SOD, GSH Px, and G6PD amount occur on the third experimental group, whose *rhodiola* extract and alpha-GPC combination ratio is 1:3. Obviously, the *rhodiola* extract and alpha-GPC combination of the present invention effectively increase the antioxidative ability of human body, so as to effectively cleanse the peroxidic molecules and free radicals. The experiment proves that the third experimental group acquires the best antioxidative effect, and is beneficial for postponing body aging.

(E) Human Growth Hormone (HGH) Variation in Blood

HGH analysis: The HGH concentration in blood is analyzed by use of human growth hormone ELISA kit

TABLE 5

HGH variations of each group of subjects

| Groups | Normal group | Control group | First experimental group | Second experimental group | Third experimental group | Fourth experimental group |
|---|---|---|---|---|---|---|
| | | | Liver homogenate biochemical values | | | |
| hGF (ng/mL) | 327.69 ± 4.0$^b$ | 316.2 ± 12.4$^a$ | 330.9 ± 6.4$^b$ | 329.3 ± 10.6$^b$ | 329.9 ± 4.5$^b$ | 330.4 ± 6.3$^b$ |

*P < 0.05,
**P < 0.01,
***P < 0.001

Referring to Table 5, HGH variation of each group of subjects are listed. Based on Table 5, after twelve weeks of experiment, the HGH variation concentration of the control group subjects are significantly lower than that of the normal group subjects (P<0.05), but the HGH variation concentrations of the subjects of first to fourth experimental groups are significantly higher than that of the control group subjects (P<0.05). To explain further, after the administration of *rhodiola* and alpha-GPC combination, the subjects that are induced for aging and obesity have higher HGH operation effectiveness, which is able to facilitate the weight reduction of the subjects.

(F) Tissue Section Staining Observation (1) After aging induction with D-galactose, hair color variation of the subjects are observed. If the subject is accordingly aging, the hair color gradually become white-colored. Therefore, a photograph record is to be kept. Referring to FIG. 1, the stained hair follicles and subcutaneous fat of skin tissue of each group of experiment subjects are illustrated. Based on FIG. 1, hair follicles of the control group subjects become loosely distributed than that of the normal group subjects. Also, thickness of subcutaneous fat of the control group subjects become higher than that of the normal group subjects. However, hair follicles of the first to fourth experimental groups become closely distributed than that of the control group subjects, and thickness of subcutaneous fat of the first to fourth experimental groups become significantly thinner.

TABLE 6 subcutaneous fat thickness variations of each group of subjects

| Groups | Normal group | Control group | First experimental group | Second experimental group | Third experimental group | Fourth experimental group |
|---|---|---|---|---|---|---|
| | | | subcutaneous fat thicknesses | | | |
| μm | 74.1 ± 19.5$^a$ | 341.9 ± 130.6$^d$ | 235.9 ± 54.2$^c$ | 167.6 ± 30.3$^b$ | 160.0 ± 46.7$^b$ | 163.5 ± 40.0$^b$ |

Referring to FIG. 1 and Table 6, it is further discovered that, compared with the first experimental group subjects that are administered with only *rhodiola* extract, the subjects of the second to fourth groups that are administered with the combination of *rhodiola* extract and alpha-GPC have the subcutaneous fat thickness which is significantly lower, wherein the greatest subcutaneous fat thickness reduction occurs on the third experimental group subjects. Therefore, the administration of the combination of *rhodiola* extract and alpha-GPC not only increases hair follicles and hair amount of the subjects, but also lower the subcutaneous fat thickness of the subjects.

Figure 2:
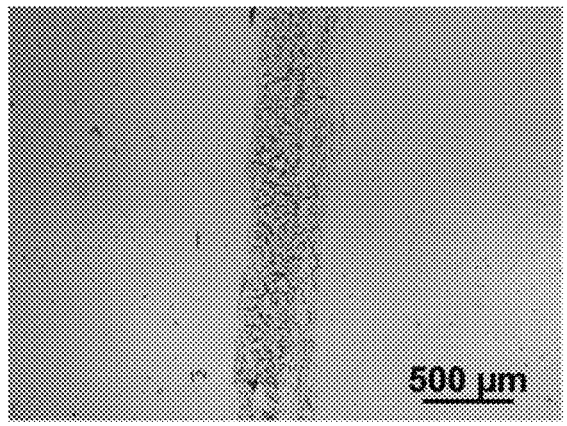
FIG. 2 is an image illustrating immunostaining of skin tissue of each group of experiment subjects.
Figure 2:
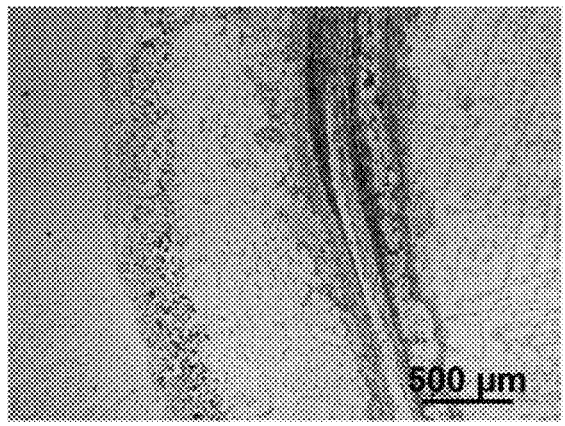
Figure 2:
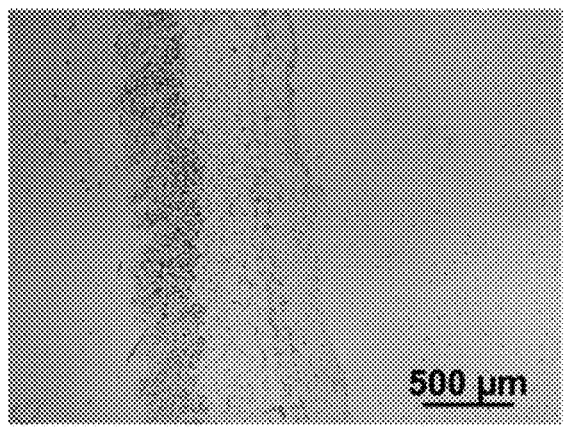
Figure 2:
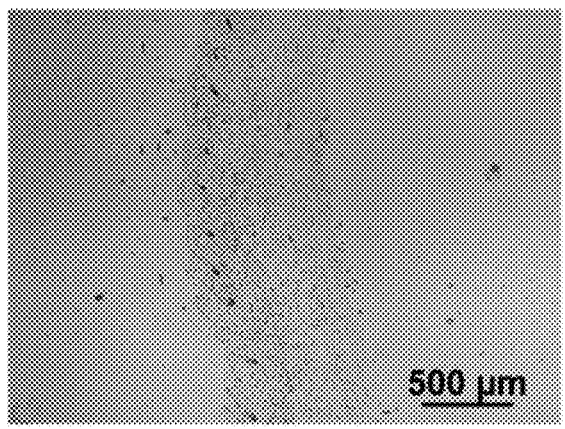
Figure 2:
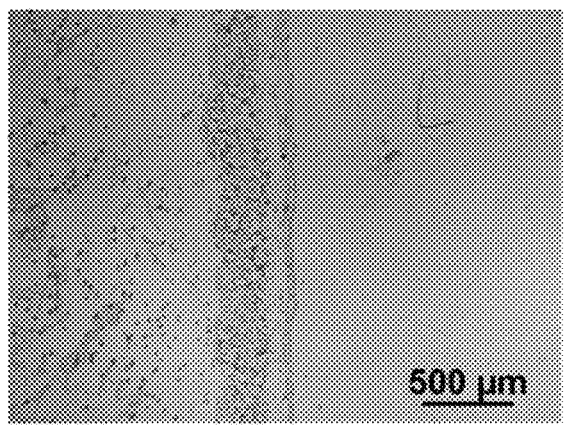
Figure 2:
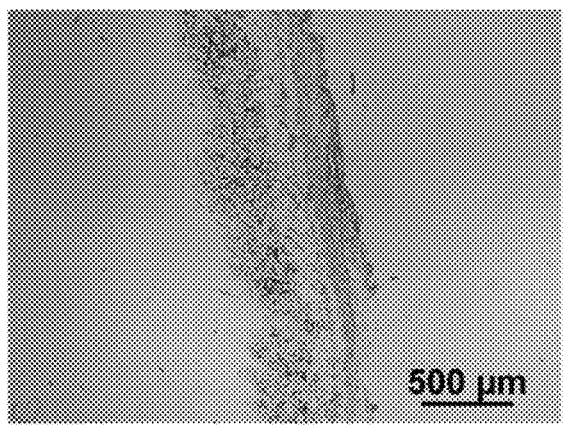

(2) The skins of each group of subjects are taken and immersed to be fixed in 10% formalin solution, so as to undergo the 4-hydroxynonenal (4-HNE) staining experiment. Notably, the subjects are injected with D-galactose are induced to have a lipid peroxidation, wherein the lipid peroxidation produce Malonaldehyde (MDA) and 4-hydroxynonenal, therefore causing the change of fluidity and permeability of cell membrane and the structure and functions of cells. Accordingly, if the color deposition detected by the 4-HNE staining is darker, it means the peroxide amount in the subject is higher. In contrast, if the color deposition detected by the 4-HNE staining is lighter, it means the peroxide amount in the subject is lesser. Referring to FIG. 2, immunostaining of skin tissue of each group of experiment subjects is illustrated.

Based on FIG. 2, compared with the color deposition detected on the normal group subjects, the color deposition detected by 4-HNE staining experiment on the control group subjects is darker, which means a serious peroxidation occurring in the control group subjects. However, the color deposition detected by 4-ENE staining experiment on the second to fourth experimental group subjects is significantly lighter than that of the control group, and the color deposition detected on the third experimental group subjects is the lightest, and the stained area of the third experimental group subjects is also the smallest. Therefore, the third experimental group subjects have the most optimal anti-peroxidation effect. Therefore, the combination of *rhodiola* extract and alpha-GPC of the present invention effectively improves the anti-peroxidation function.

To sum up, the combination of the present invention is allowed to be used for treating obesity by orally administering the combination of *rhodiola* extract and alpha-GPC to the subjects. The combination is able to restrain the body fat formation and effectively reduce the weight and body fat of the subjects, and also improve the anti-peroxidation function for achieving the aging postponing effect. Therein, when the ratio between the *rhodiola* extract and the alpha-GPC is 1:3, the combination achieves the best effect on restraining body fat formation, reducing body weight, and anti-oxidizing.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. An antioxidative activity promoting composition, comprising an effectively dosage amount of a *rhodiola* extract, an alpha-GPC, and a pharmaceutically acceptable vehicle or salt thereof, wherein a weight ratio between the *rhodiola* extract and the alpha-GPC ranges from 1:1 to 1:6.

2. The composition of claim 1, wherein an effectively dosage amount of the composition ranges from 187 to 680 mg/kg bw per day.

3. The composition of claim 1, wherein the weight ratio between the *rhodiola* extract and the alpha-GPC is 1:3.

4. The composition of claim 3, wherein an effectively dosage amount of the composition is 384 mg/kg bw per day.

5. The composition of claim 1, further comprising a resveratrol.

6. The composition of claim 5, further comprising a guarana content.

7. The composition of claim 6, wherein the composition is prepared in a capsule form.

8. The composition of claim 1, wherein the composition is prepared in a form selected from a group consisting of powder form, granular form, and liquid faun.

9. A method for treating obesity with the composition of claim 1, including a step of orally administering an effectively dosage amount of the composition to a subject, such that the composition including the *rhodiola* extract and the alpha-GPC restrains a body formation of the subject and promotes an antioxidative activity of the subject.

* * * * *